(12) United States Patent
Yao et al.

(10) Patent No.: US 9,156,755 B2
(45) Date of Patent: Oct. 13, 2015

(54) CONVERTING GLYCOLS TO ALCOHOLS

(71) Applicant: Phillips 66 Company, Houston, TX (US)

(72) Inventors: Jianhua Yao, Bartlesville, OK (US); Edward L Sughrue, II, Bartlesville, OK (US); TiePan Shi, Bartlesville, OK (US); Brian Dunn, Bartlesville, OK (US)

(73) Assignee: PHILLIPS 66 COMPANY, Houston, TX (US)

( * ) Notice: Subject to any disclaimer, the term of this patent is extended or adjusted under 35 U.S.C. 154(b) by 48 days.

(21) Appl. No.: 13/771,169

(22) Filed: Feb. 20, 2013

(65) Prior Publication Data

US 2013/0219778 A1 Aug. 29, 2013

Related U.S. Application Data

(60) Provisional application No. 61/604,287, filed on Feb. 28, 2012.

(51) Int. Cl.
*C07C 29/60* (2006.01)
*C07C 29/17* (2006.01)

(52) U.S. Cl.
CPC ............... *C07C 29/175* (2013.01); *C07C 29/60* (2013.01)

(58) Field of Classification Search
CPC .............................. C07C 29/175; C07C 29/60
USPC ...................................... 568/902; 44/452, 451
See application file for complete search history.

(56) References Cited

U.S. PATENT DOCUMENTS

| | | | |
|---|---|---|---|
| 2,947,739 A * | 8/1960 | Gaslini | ......................... 530/503 |
| 5,180,868 A | 1/1993 | Baker et al. | |
| 6,306,287 B1 | 10/2001 | Billion et al. | |
| 6,387,248 B2 | 5/2002 | Sherwood, Jr. et al. | |
| 6,686,487 B2 | 2/2004 | Franks | |
| 6,982,328 B2 * | 1/2006 | Werpy et al. | .................. 536/128 |
| 7,550,634 B2 | 6/2009 | Yao et al. | |
| 2009/0054701 A1 * | 2/2009 | Abhari | ......................... 568/861 |

FOREIGN PATENT DOCUMENTS

GB 1109556 4/1968

OTHER PUBLICATIONS

Wojcik, et al., "Hydrogenolysis of Alcohols to Hydrocarbons," J. Am. Chem. Soc., 55(3), 1293-1294, 1933.*
Mielenz, "Ethanol production from biomass: technology and commercialization status," Current Opinion in Microbiology, 4, 324-329, 2001.*
He et al., "Hydroxygenation of model compounds and catalytic systems for pyrolysis bio-oils upgrading," Catalysis for Sustainable Energy, 28-52, 2013.*
"Fast Pyrolysis Bio-Oil and Its Upgrading", 96 pages.
Eddie G. Baker and Douglas C. Elliot, "Catalytic Hydrotreating of Biomass-Derived Oils", Pacific Northwest Laboratory, pp. 257-263.
D.C. Elliot and E.G. Baker, "Hydrotreating Biomass Liquids to Produce Hydrocarbon Fuels" (Abstract), 1986, Energy Citations Database, 2 pages.
Paper: Guillena, G. et al.—Chem. Rev. 2010, 110, 1611-1641.
Paper: Lee, A. F. et al.—J. Phys. Chem. Lett. 2007, 111, 18844-18847.
Paper: Celenligil-Cetin, R. et al.—Organometallics, 2005, 24, 186-189.
Paper: Bowker, M. et a.l—J. Phys. Chem. 2010 (in press).
Paper: Krafft, M. E. et al—J. Org. Chem. 1988, 53, 3158-3163.
Paper: Baker and Elliott, Pacific Northwest Laboratory, Richland, WA 99352.
"Hydrotreating biomass liquids to produce hydrocarbon fuels." Elliot and Baker. Conference: 10. Annual symposium on energy from biomass and wastes, Washington, DC, USA, Apr. 7, 1986.
"Hydrodeoxygenation of Wood-Derived Liquids to Produce Hydrocarbon Fuels"—Elliott and Baker, SAE Paper No. 859096 Presented at 20th IECEC Meeting, Miami Beach, 1985 Society of Automotive Engineers: Warrenton, PA, 1985; vol. 1, pp. 586-594.

\* cited by examiner

*Primary Examiner* — Fereydoun G Sajjadi
*Assistant Examiner* — Mark Luderer
(74) *Attorney, Agent, or Firm* — Phillips 66 Company

(57) ABSTRACT

The conversion of diols to mono-alcohols as fuel blendstocks. In one embodiment hydrotreating processes are described that selectively convert glycols to mono-alcohols that can be blended as biofuels. Both NiMo and CoMo catalysts are active for the reaction and reaction conditions can also impact the selectivity of mono-alcohols.

7 Claims, No Drawings

CONVERTING GLYCOLS TO ALCOHOLS

CROSS-REFERENCE TO RELATED APPLICATIONS

This application is a non-provisional application which claims the benefit of and priority to U.S. Provisional Application Ser. No. 61/604,287 filed Feb. 28, 2012, entitled "Converting Glycols to Alcohols," which is hereby incorporated by reference in its entirety.

STATEMENT REGARDING FEDERALLY SPONSORED RESEARCH OR DEVELOPMENT

None.

FIELD OF THE INVENTION

The conversion of diols to mono-alcohols as fuel blendstocks. In one embodiment hydrotreating processes are described that selectively convert glycols to mono-alcohols that can be blended as biofuels. Both NiMo and CoMo catalysts are active for the reaction and reaction conditions can also impact the selectivity of mono-alcohols.

BACKGROUND OF THE INVENTION

Cellulose and hemicellulose are two major constitutes in the biomass and can be broken down to C6 and C5 sugars using acid or enzyme hydrolysis processes.

Furthermore, diols can be derived from C6 and C5 sugars via hydrogenolysis. For example, ethylene glycol and propylene glycol can be derived from biomass, as demonstrated by U.S. Pat. No. 6,982,328.

C2-C6 diols from ethylene glycol to hexanediol cannot serve as fuel components as they are immiscible with hydrocarbon yet miscible with water. To convert them to fuel molecules, complete hydrotreating is not a desired process as the final products are light hydrocarbons which are of limited use in the gasoline blending pool, especially for ethane and propane. However, mono alcohols are legitimate gasoline blendstocks that can be produced by partial hydrogenation of the diols.

BRIEF SUMMARY OF THE DISCLOSURE

This invention relates to the conversion of diols to mono-alcohols as fuel blendstocks. C2-C6 mono-alcohols are legitimate fuel blending molecules as they generally possess good octane rating and low vapor pressure (except ethanol in E10). The added benefit is at least 50% lower hydrogen consumption compared to complete hydrogenation.

In one embodiment, producing mono-alcohols from glycols is described where a biomass derived glycol feed provided; the glycol feed is partially hydrogenated with a hydrogenation catalysts to produce a mono-alcohol, where the hydrogenation reaction occurs at a temperature and pressure that selectively deoxygenates one of the two hydroxyls, one or more mono-alcohols are isolated, unreacted glycol is recycled to the glycol feed, and the mono-alcohol is blended in a fuel.

In another embodiment, the glycol feedstock comprises one or more glycols including glycol, methanediol, ethylene glycol, propylene glycol, butanediol, pentanediol, hexanediol, cyclohexanediol, septanediol, octanediol, decanediol, benzenediol, etohexadiol, methyl-propanediol, methyl-pentanediol, 1,3-propanediol, 1,6-hexanediol, 1,4-pentanediol, 1,5-hexanediol, 1-methoxy-2-propanol, 1,2-butanediol, 1,3-butanediol, 2,3-butanediol, 1,4-butanediol, 2-methyl-1,2-propanediol, dimethylolpropane, amylene glycol, 1,2-pentanediol, 1,3-pentanediol, 1,4-pentanediol, 1,5-pentanediol, 2,3-pentanediol, 2,4-pentanediol, 2,5-hexanediol, hexylene glycol, tetramethylene glycol, 1,7-heptanediol, 1,8-octanediol, 1,10-decanediol, 2-ethyl-1,3-hexanediol, benzenedimethanol, phenyl-ethanediol and styrene glycol.

In one embodiment, the hydrogenation catalyst may be nickel (Ni), cobalt (Co), molybdenum (Mo), ceria (Ce), magnesium (Mg), gold (Au), iridium (Ir), osmium (Os), palladium (Pd), platinum (Pt), rhodium (Rh), ruthenium (Ru), tungsten (W), titanium (Ti), NiMo, CoMo, NiW, CoW, Ru, Pt, Pd, and combinations thereof. The hydrogenation catalyst may be supported or unsupported. A supported hydrogenation catalyst may be supported by silica, alumina, silica alumina, zeolite, activated carbon, and combinations thereof. Additionally the catalyst may be sulfided prior to hydrogenation.

In one embodiment the hydrotreating reaction occurs at temperatures between approximately 50 and 350° C., including approximately 50° C., 75° C., 100° C., 125° C., 150° C., 160° C., 170° C., 180° C., 190° C., 193° C., 200° C., 210° C., 220° C., 225° C., 250° C., 254° C., 258° C., 260° C., 275° C., 280° C., 290° C., 292° C., 293° C., 300° C., 310° C., 320° C., 330° C., 340° C., or 350° C.

Additionally the hydrotreating reaction may occurs at pressures between approximately 100 and 2000 psig, including approximately 100 psig, 170 psig, 200 psig, 300 psig, 400 psig, 500 psig, 600 psig, 700 psig, 800 psig, 900 psig, 1000 psig, 1100 psig, 1200 psig, 1300 psig, 1400 psig, 1500 psig, 1600 psig, 1700 psig, 1800 psig, 1900 psig or 2000 psig.

Alternatively, in another embodiment the biomass derived glycol feed is cofed with a hydrocarbon feed selected from crude oil, diesel, vacuum oil, distillates, naphtha, or other readily available hydrocarbon feed.

BRIEF DESCRIPTION OF THE DRAWINGS

None

DETAILED DESCRIPTION

C6 and C5 sugars can be further converted to glycols, such as ethylene glycols and propylene glycols, via a hydrogenolysis reaction. It is now found that commercial hydrotreating catalysts, such as CoMo or NiMo, can selectively convert glycols to mono-alcohols. In addition, reaction conditions played an important role in terms of increasing mono-alcohol selectivity and catalyst life.

The tests were conducted on a laboratory fixed-bed hydrotreating apparatus using NiMo and CoMo catalysts. NiMo, CoMo, and other hydrotreating catalysts are available from a variety of commercial suppliers including Albermarle, BASF, ChinaCatalyst, Haldor-Topsoe, Nippon-Ketjen, Tri-Cat, UniCat, UOP. For more information on hydrotreating catalysts see Coulier, 2001. Additionally, these catalysts may be prepared by precipitation with or without a substrate.

Catalysts were combined with 30/40 mesh quartz particles before being packed in the middle section of a ¾" OD reactor. The remaining volume of the reactor was packed with inert alundum. The NiMo and CoMo catalysts were initially sulfided. Typical reaction conditions were 800 psig and 300 sccm hydrogen. A high-boiling diluent (ultra low sulfur diesel from Borger U19.3 with addition of 400 ppm sulfur in the form of dimethyl disulfide) was used in a subset of the tests.

The following examples of certain embodiments of the invention are given. Each example is provided by way of explanation of the invention, one of many embodiments of the invention, and the following examples should not be read to limit, or define, the scope of the invention.

EXAMPLE 1

Ethylene Glycol Conversion

Table 1 below illustrated that both CoMo and NiMo catalyst are active for converting ethylene glycol to ethanol.

TABLE 1

Conversion of Ethylene Glycol to Ethanol

| | | | |
|---|---|---|---|
| T (° C.) | | 260 | 258 |
| P, psig | | 800 | 800 |
| Catalyst | | CoMo (5 ml) | NiMo (5 ml) |
| Feed: | $H_2$, ml/min | 300 | 300 |
| | Ethylene Glycol, ml/hr | 18 | 18 |
| | Diesel, ml/hr | 18 | 18 |
| Ethylene Glycol Conversion, % | | 42% | 71% |
| Ethanol Selectivity, C % | | 50% | 29% |

As demonstrated, both the CoMo and NiMo hydrotreating catalyst were able to generate between approximately 30 to 50% ethanol from ethylene glycol. Ethanol is miscible with gasoline, diesel, jet-fuel, and other fuel oils up to 10 to 80% for E10 or E80 fuels.

EXAMPLE 2

Ethylene Glycol Partial Hydrogenation With Diesel Co-Feed

With increased space velocity and reduced temperature, as shown in Table 2, lower ethylene glycol conversion and higher ethanol selectivity was observed.

TABLE 2

Conversion of Ethylene Glycol to Ethanol with a Diesel Co-Feed

| T, C. | 260 | 292 | 293 | 293 | 293 | 293 |
|---|---|---|---|---|---|---|
| P, psig | 800 | 800 | 800 | 300 | 300 | 170 |
| $H_2$, ml/min | 300 | 300 | 300 | 300 | 300 | 300 |
| Ethylene Glycol, ml/hr | 18 | 18 | 6 | 6 | 6 | 6 |
| Diesel, ml/hr | 18 | 18 | 18 | 18 | 6 | 6 |
| Ethylene Glycol Conversion % | 42% | 78% | 96% | 80% | 99% | 95% |
| Ethanol Selectivity, C % | 50% | 15% | 13% | 34% | 34% | 40% |

Table 2 showed that reaction conditions can significantly impact the ethylene glycol conversion and ethanol selectivity. Reducing reaction pressure increases ethanol selectivity, but decrease ethylene glycol conversion. Similar observation was found with reaction temperature was reduced from 292 C to 260 C. These tests were carried out over a CoMo catalyst (5 ml).

In closing, it should be noted that the discussion of any reference is not an admission that it is prior art to the present invention, especially any reference that may have a publication date after the priority date of this application. At the same time, each and every claim below is hereby incorporated into this detailed description or specification as an additional embodiment of the present invention.

Although the systems and processes described herein have been described in detail, it should be understood that various changes, substitutions, and alterations can be made without departing from the spirit and scope of the invention as defined by the following claims. Those skilled in the art may be able to study the preferred embodiments and identify other ways to practice the invention that are not exactly as described herein. It is the intent of the inventors that variations and equivalents of the invention are within the scope of the claims while the description, abstract and drawings are not to be used to limit the scope of the invention. The invention is specifically intended to be as broad as the claims below and their equivalents.

REFERENCES

All of the references cited herein are expressly incorporated by reference. The discussion of any reference is not an admission that it is prior art to the present invention, especially any reference that may have a publication data after the priority date of this application. Incorporated references are listed again here for convenience:

1. GB1109556, Shell Int. Research, "Process for the Hydrogenative Treatment of Hydrocarbon Oils" Apr. 10, 1968.
2. U.S. Pat. No. 5,180,868, Baker et al., Method of Upgrading Oils Containing Hydroxyaromatic Hydrocarbon Compounds to Highly Aromatic Gasoline" (Jan. 19, 1993)
3. U.S. Pat. No. 6,306,287, Billon et al., Process for Hydrotreatment of a Heavy Hydrocarbon Fraction Using Permutable Reactors and Introduction of a Middle Distillate" (Oct. 23, 2001).
4. U.S. Pat. No. 6,387,248, Sherwood, Jr., et al., "Method of Preparing a Catalyst for use in the Hydrotreating of High Boiling Hydrocarbon Feedstocks" May 14, 2002.
5. U.S. Pat. No. 6,686,487, Franks, "Triacylglycerol Oligomer Products and Methods of Making Same", Feb. 3, 2004.
6. U.S. Pat. No. 7,550,634, Yao, et al., "Process for Converting Triglycerides to Hydrocarbons", Jun. 23, 2009.
7. "Fast Pyrolysis Bio-Oil and Its Upgrading," Pacific National Laboratory (PNNL) 119, 126-128, 138-140, the Univ. of Louvian (UCL) 141-146, and the Institute of Wood Chemistry (Germany) 129.
8. Baker and Elliot, "Catalytic Hydrotreating Of Biomass-Derived Oils,"
9. Elliott and Baker, "Hydrodeoxygenation of Wood-Derived Liquids to Produce Hydrocarbon Fuels." SAE Paper No. 859096 Presented at 20th IECEC Meeting, Miami Beach, 1985 Society of Automotive Engineers: Warrenton, Pa., 1985; Vol. 1, pp 586-594.
10. Ethanolproducer.com Web Site. http://www.ethanolproducer.com/article.jsp?article_id=6586 (accessed Aug. 1, 2010).
11. Werpy, T. A. et al. Methods of Producing Compounds from Plant Material. U.S. Pat. No. 6,982,328, Jan. 3, 2006.
12. Guillena, G.; Ramon, D. J.; Yus, M. Chem. Rev. 2010, 110, 1611-1641.
13. Lee, A. F.; Chang, Z.; Ellis, P.; Hackett, S. F. J.; Wilson, K. J. Phys. Chem. Lett. 2007, 111, 18844-18847.
14. Celenligil-Cetin, R.; Watson, L. A.; Guo, C.; Foxman, B. M.; Ozerov, O. V. Organometallics, 2005, 24, 186-189.
15. Bowker, M.; Gilbert, L.; Counsell, J.; Morgan, C. J. Phys. Chem. 2010 (in press).
16. Krafft, M. E.; Crooks, W. J.; Zorc, B.; Milczanowski, S. E. J. Org. Chem. 1988, 53, 3158-3163.
17. Chen, Y.-Z.; Chan, W. C.; Lau, C. P.; Chu, H. S.; Lee, H. L. Organometallics, 2005, 24, 186-189.
18. Coulier, "Hydrotreating Model Catalysts: from characterization to kinetics" Doctorate Thesis, Technische Universiteit Eindhoven (2001).

The invention claimed is:

1. A method of producing mono-alcohols from glycols comprising:
    a) providing a biomass derived glycol feed, wherein said glycol feed comprises one or more glycols selected from the group consisting of methanediol, ethylene glycol, propylene glycol, butanediol, pentanediol, hexanediol, cyclohexanediol, septanediol, octanediol, decanediol, benzenediol, etohexadiol, methyl-propanediol, methyl-pentanediol, 1,3-propanediol, 1,6-hexanediol, 1,4-pentanediol, 1,5-hexanediol, 1-methoxy-2-propanol, 1,2-butanediol, 1,3-butanediol, 2,3-butanediol, 1,4-butanediol, 2-methyl-1,2-propanediol, dimethylolpropane, amylene glycol, 1,2-pentanediol, 1,3-pentanediol, 1,4-pentanediol, 1,5-pentanediol, 2,3-pentanediol, 2,4-pentanediol, 2,5-hexanediol, hexylene glycol, tetramethylene glycol, 1,7-heptanediol, 1,8-octanediol, 1,10-decanediol, 2-ethyl-1,3-hexanediol, bis(hydroxymethyl)benzene, phenyl-ethanediol and styrene glycol;
    b) partially hydrogenating the glycol feed with a hydrogenation catalyst to produce a mono-alcohol, wherein said hydrogenation reaction occurs at a temperature and pressure that selectively deoxygenates one of the two hydroxyls, wherein said hydrogenation catalyst comprises molybdenum (Mo) and at least one metal selected from nickel (Ni) and cobalt (Co);
    c) isolating one or more of said mono-alcohol;
    d) recycling unreacted glycol to (a), and
    e) blending said mono-alcohol in a fuel.

2. The method of claim 1, wherein said hydrogenation catalyst is unsupported.

3. The method of claim 1, wherein said hydrogenation catalyst is supported by silica, alumina, silica alumina, zeolite, activated carbon, or combinations thereof.

4. The method of claim 3, wherein said hydrogenation catalyst is sulfided prior to said hydrogenation reaction.

5. The method of claim 1, wherein said hydrogenation reaction occurs at a temperature between approximately 50° C. and 350° C.

6. The method of claim 1, wherein said hydrogenation reaction occurs at a pressure between approximately 100 and 2000 psig.

7. The method of claim 1, wherein said biomass derived glycol feed is co-fed with a hydrocarbon feed selected from crude oil, diesel, vacuum oil, distillates, naphtha, or other hydrocarbon feed.

* * * * *